United States Patent [19]

Wood et al.

[11] 4,088,132
[45] May 9, 1978

[54] HYDROPHILIC POLYURETHANE FOAMS FOR USE IN CATAMENIAL DEVICES

[75] Inventors: Louis L. Wood, Rockville, Md.; Jerome L. Murray, New York, N.Y.; Frances R. Gardiner, Sparta, N.J.

[73] Assignee: W. R. Grace & Co., New York, N.Y.

[21] Appl. No.: 575,356

[22] Filed: May 7, 1975

[51] Int. Cl.² ............................................. A61F 13/20
[52] U.S. Cl. .................................... 128/285; 128/270
[58] Field of Search ................ 128/270, 284, 285, 290

[56] References Cited

U.S. PATENT DOCUMENTS

| | | | |
|---|---|---|---|
| 1,575,123 | 3/1926 | Martucci-Pisculli | 128/270 |
| 2,386,590 | 10/1945 | Calhoun | 128/270 |
| 2,690,415 | 9/1954 | Shuler | 128/290 R |
| 2,808,832 | 10/1957 | Myers et al. | 128/285 |
| 3,306,966 | 2/1967 | Matejcek et al. | 128/285 X |
| 3,515,138 | 6/1970 | Hochstrasser et al. | 128/285 X |
| 3,595,236 | 7/1971 | Corrigan et al. | 128/285 |
| 3,670,731 | 6/1972 | Harmon | 128/284 |
| 3,690,321 | 9/1972 | Hirschman | 128/285 |
| 3,765,417 | 10/1973 | Crockford | 128/285 X |
| 3,900,030 | 8/1975 | Bashan | 128/285 |

Primary Examiner—Stephen C. Pellegrino
Attorney, Agent, or Firm—Mel K. Silverman; David A. Jackson; Richard M. Goldberg

[57] ABSTRACT

A hydrophilic polyurethane foam for use in a catamenial device such as a tampon is disclosed which can be compressed to less than about 50 percent of its original dry volume, stored in such condition for an extended period of time, and later rapidly re-expanded to at least its dry volume. Prior to compression, the foam is impregnated with a solid inorganic release agent, which is located within the cells of the foam and maintains the separation of the cell walls. Adherence of contiguous cell walls is prevented and the rapid re-expansion of the foam upon contact with moisture or water is thereby facilitated.

13 Claims, 5 Drawing Figures

HYDROPHILIC POLYURETHANE FOAMS FOR USE IN CATAMENIAL DEVICES

BACKGROUND OF THE INVENTION

This invention generally relates to hydrophilic polymeric foam materials which can be placed in compression for an extended period of time and then rapidly re-expanded in contact with water or moisture. This invention is particularly concerned with re-expandable hydrophilic foams possessing utility in catamenial devices such as a tampon assembly.

Polymeric foam materials have been compressed and subsequently re-expanded by various methods in the art. One such method comprises treating the foam with a suitable adhesive to maintain the foam in a compressed state, and, when desired, removing the adhesive by means of a solvent to re-expand the foam. Another common method comprises incorporating a material, solid at normal temperatures but liquid at elevated temperatures, into the foam. In this technique, the material is impregnated into the foam as a liquid, the foam compressed and subsequently cooled. Upon reheating the foam to the range of the melting point of the impregnated material, the foam then re-expands.

The above techniques both possess the shortcoming that the re-expansion of the foam is comparatively slow. That is, in the uses to which such foams have largely been directed, no requirement has existed that the foam re-expand rapidly. In addition, foam materials held in compression by the above methods, and thereby reduced in volume for extended periods of time, tend to remain at the reduced volume even after the compressive force is removed. This condition is known as compression set or fatigue, and is particularly deleterious in the instance where the foam is to serve in a liquid absorbing capacity, such as in a catamenial tampon assembly, and where the useful volume of the foam must, if anything, exceed that of the original shape. If employed in a tampon, the foam must re-expand as rapidly as possible to prevent the escape of menstrual fluids from the vagina, a phenomenon known as bypass. Reliance either upon body fluid as a solvent for an adhesive, or the use of body heat to melt an impregnated agent is too time consuming. Too much time is required for body moisture and/or body heat to fully permeate the compressed foam in order to cause re-expansion.

An additional method to provide a compressed, re-expandable foam is disclosed in U.S. Pat. No. 3,306,966, to Matejcek et al. In this reference, the foam is impregnated with a defatiguing agent and a fixating agent. The defatiguing agents are liquid, water soluble substances such as polyethylene glycol. The foam is either coimpregnated or coated with a fixating agent. The fixating agent maintains the compressed foam containing the defatiguing agent in the compressed condition until it is dissolved away or its effect removed by exceeding its melting point. The function of the defatiguing agent is to aid the foam in regaining its original volume when later re-expanded. While the foams so treated tended to exhibit reduced fatigue or compression, the regularity of extent of expansion particularly required for catamenial purposes was lacking. This was believed to be due to the water solubility of the fatiguing agent, which failed to be uniformly entrained by the foam during impregnation, and could be easily expelled during the removal of excess solution.

SUMMARY OF THE INVENTION

In accordance with the present invention, a hydrophilic polymeric foam is prepared which can be compressed and maintained in that condition for a prolonged period of time, and rapidly re-expanded using water or moisture. The foam is impregnated with a particulate, water insoluble, inorganic solid material prior to compression. This solid agent is uniformly entrained within the foam cell structure and keeps the cell walls sufficiently apart while the foam is compressed so that when subsequently contacted with water, the hydrophilic cell surfaces rapidly take up the water or moisture and cause the foam to expand to at least its dry volume. In addition to being rapid, expansion is complete and uniform, and to a maximum volume usually in excess of the original shape prior to compression. The solid agent, thus, keeps the cell walls apart so that a physical or physical-chemical bond will not form during compression, and facilitates accelerated water uptake which results in the rapid re-expansion of the foam.

The polymeric foam of this invention, may be compressed and stored for an extended period of time by a variety of constraining means. When the compressed foam is used as a tampon, a constraining means such as a gelatin capsule may be employed which substantially encases the foam prior to insertion. The capsule helps to protect the compressed foam from contact with moisture before use, and also serves as a lubricant during tampon insertion. Upon insertion, the capsule quickly dissolves to release the foam which then expands in a comparatively rapid and uniform manner into leak-proof contact with the vaginal periphery.

It is a principal object of the present invention to provide a hydrophilic polymeric foam which may be maintained in compression for an extended period of time and then rapidly re-expanded to at least its original volume.

It is a further object of the present invention to provide hydrophilic polymeric foam impregnated with a solid water insoluble agent which facilitates its rapid re-expansion from a state of compression upon contact with moisture or water.

It is still a further object of the present invention to provide a hydrophilic foam as aforesaid which is held in compression by a constraining means such as a gelatin capsule.

It is yet a further object of the present invention to provide a hydrophilic foam as aforesaid in a catamenial device such as a tampon which rapidly expands to prevent menstrual bypass.

Other objects and advantages will be apparent to those skilled in the art from a consideration of the detailed description which follows with reference to the accompanying figures.

DETAILED DESCRIPTION

Figure 1:
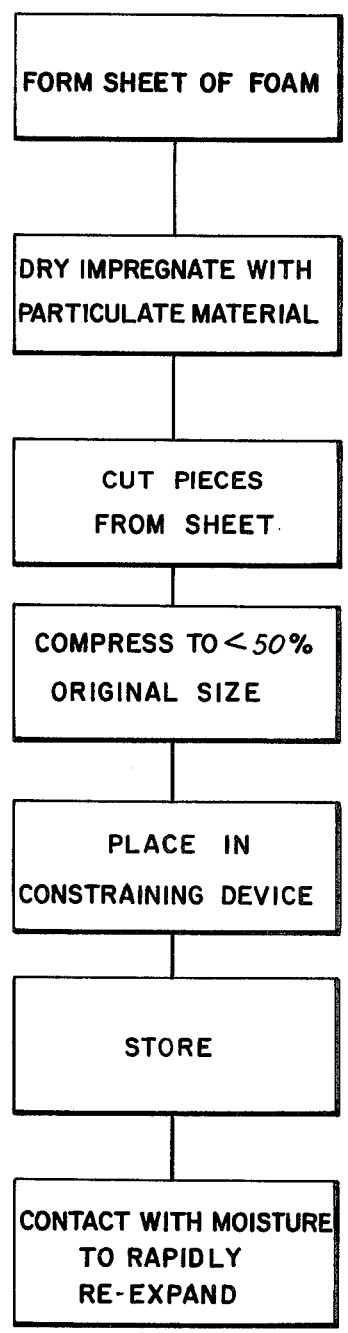
FIG. 1 is a flow diagram outlining the preparation of the foam in accordance with this invention employing a dry impregnation technique.

In accordance with the present invention, a hydrophilic polymeric foam is prepared which possesses an improved ability to re-expand after sustaining prolonged compression, by impregnation with a particulate, solid inorganic water insoluble material. The foams so treated possess particular utility in catamenial devices such as a tampon assembly.

The polymeric foams of the present invention may be hydrophilic polyurethane foams or hydrophilic formaldehyde polyvinylalcohol foams. It is preferred, however, that the foam be a hydrophilic polyurethane foam. A commercially available hydrophilic polyurethane foam is marketed under the tradename Acquell ® and is available from the Scott Paper Company. This is a polyurethane foam produced by the reaction of a polyesterdiol and tolylene diisocyanate. The polyesterdiol also contains adipic acid and block copolymers of polyoxyethylene and polyoxypropylene.

Another foam which may be used in accordance with this invention, is prepared by, in a first step, forming a prepolymer by the reaction of polyethylene glycol and trimethylol propane in a mole ratio of about 2:0.125 to 2:2 respectively, followed by capping the reaction product at all hydroxy locations using tolylene diisocyanate consisting of about an 80/20 mixture of the 2,4 isomer to 2,6 isomer; and in a second step reacting 100 parts by weight of prepolymer with 30 parts by weight of water containing 5 parts by weight of a polyoxyalkylene nonionic surfactant. A particular non-ionic surfactant which has been found useful is one commercially available under the tradename Pluronic L-64 from the Wyandotte Chemicals Corporation. Although the above comprise the preferred hydrophilic urethane foam materials, other useful hydrophilic urethane foams are produced by varying the above prepolymer to water ratio, as well as varying the water to surfactant ratio. Polymeric foams which are to be employed in the preparation of a tampon assembly should preferably possess a maximum density of about 2.5 lbs./ft.$^3$, as difficulties arise in the compression and encapsulation of foams whose density exceeds this level.

In accordance with the method of this invention, the foam which may be formulated in the above manner is impregnated with a particulate, solid, inorganic, water insoluble material which will function to keep the cell walls apart while the foam is in a compressed state. The useful inorganic materials include talc, silica, alumina, clay, aluminosilicate, mica, soapstone, asbestos, magnesia, carbon black and baryte. These materials should preferably have an average particle size of about 0.01 to 100 microns. They are preferably impregnated into the foam in an amount of about 10 to 200 percent by weight of the foam by either dry or wet impregnation methods. Dry impregnation comprises passing an air stream carrying the solid particulate agent through the foam, whereby the foam acts in the manner of a filter and entrains the solid particulate agent. Wet impregnation comprises forming an aqueous slurry of the solid particulate agent and contacting the foam with an excess amount of slurry. The slurry may be caused to flow by means of gravity and/or may be drawn by reduced pressure into the foam. Most of the water will pass through the foam, and any remaining water can be expressed from the foam by a mild compressing. The foam can then be dried by any conventional technique such as by passing a flow of warm air therethrough.

FIG. 1 is a flow sheet of successive steps for dry impregnation of the foam and the production of articles such as tampons. The hydrophilic foam is formed into a sheet of essentially any reasonable dimensions. For use as a tampon the foam will be formed in a thickness of about 2 inches. The foam sheet is then placed in a chamber and an air stream containing the inorganic solid particulate material is drawn through the foam. The cells of the foam act as a filter and trap most of the solid agent. When the foam contains 10 to 200 percent by weight of the solid agent, it is removed from the air chamber. At this stage, in the manufacture of tampons, the sheet will be cut into individual segments of about 1 inch square. If larger articles are to be manufactured which utilize an entire sheet of foam, or if the foam is initially prepared by a molding process, such as extrusion of a finite length, which yields the ultimately desired shape, this step is eliminated.

After impregnation, and, if necessary, cutting, the foam is compressed to less than 50 percent of its original volume. In a preferred embodiment which is useful in tampon manufacture, the foam may be compressed from about less than 25 to about less than 10%. Any conventional type of press or device may be used. This operation may also be in combination with that of placing the compressed foam into the constraining device. As previously discussed, a preferred constraining device for a tampon is a gelatin capsule or cylinder. The foam piece, which measures about 1 × 1 × 2 inches, can be compressed and placed within the capsule in a single step by any of the many known techniques. One useful technique is to have a cylindrical mold of the same interior diameter as that of the capsule or with sidewalls moveable to such a diameter, which cooperates with a ram which axially thrusts into the mold cavity and forces the foam into the capsule.

The draw string conventionally attached to the tampon may be stitched into place at any time, either to the foam before encapsulation, or to the encapsulated tampon, itself. Once placed in the capsule, the foam can be stored indefinitely. As discussed earlier, the gelatin capsule readily dissolves upon contact with moisture, and the foam rapidly expands to contact the vaginal periphery.

Figure 2:
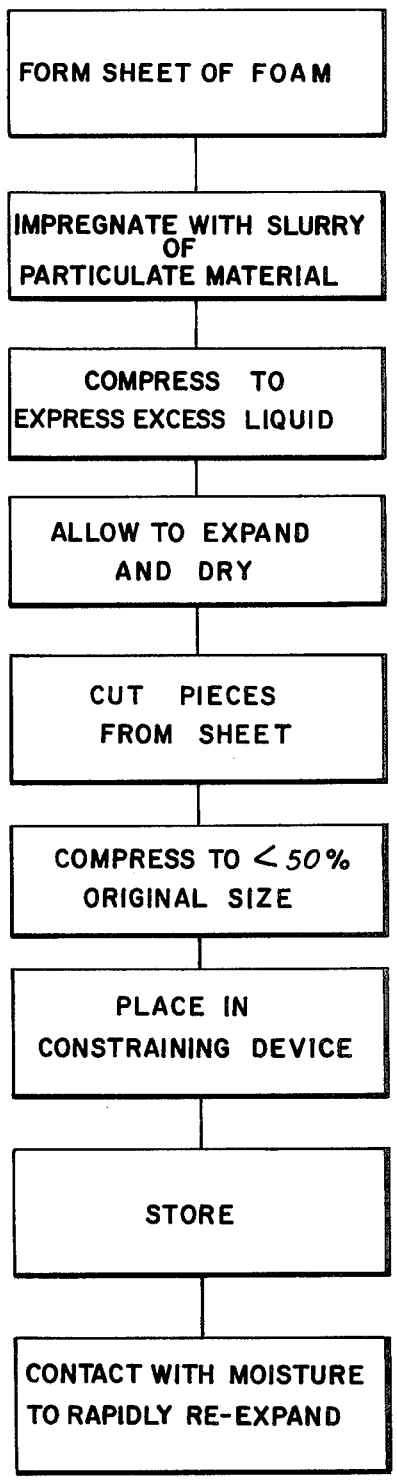
FIG. 2 is a flow diagram similar to FIG. 1 which outlines an alternate method employing a wet impregnation technique.

The embodiment of FIG. 2 is similar to that of FIG. 1, with the exception that the hydrophilic foam is impregnated with a slurry of the solid particulate agent. In this method, the foam is formed as in the method of FIG. 1. An aqueous slurry of the solid particulate material having a solids content of about 5 to 30 percent by weight if flowed onto the foam. If the slurry is sufficiently dilute, impregnation may take place simply by the action of gravity flow. If the slurry is of a concentrated nature, however, impregnation is expeditiously conducted with the application of an external force, such as increased pressure or vibration, or the application of a partial vacuum on the underside of the foam. Optionally, water may be sprayed onto the foam to get effective impregnation. At the point that solid particulate matter is drawn through the foam, the impregnation is complete. Excess liquid is then expressed from the foam by a mold compression of the foam between pinch rolls or the equivalent. The foam is then dried in a low temperature oven or the equivalent. The remaining steps of this scheme are the same as for FIG. 1.

Figure 3:
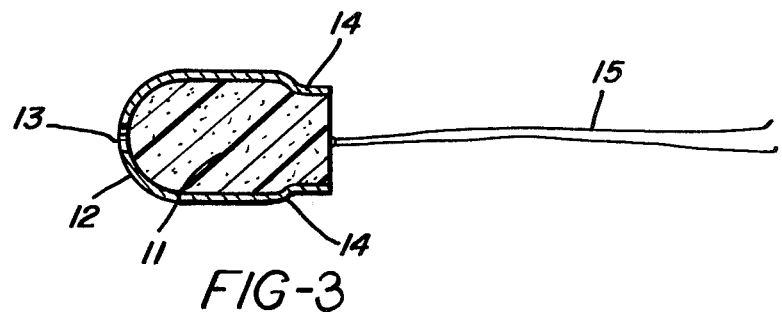
FIG. 3 is a side sectional view of a tampon comprising the foam of this invention constrained within a gelatin capsule.

FIG. 3 illustrates the rapidly re-expandable foam of this invention used as a tampon. In this illustration, draw string 15 has been attached to the foam prior to being compressed. The foam 11 is within gelatin capsule 12. The capsule preferably has an opening 13 of about ⅛ to ¼ inch diameter at the front portion and a necked region 14 at the rear portion. Opening 13 assists in the expansion of foam 11 as it provides a point of direct contact with the menstrual flow. Necked region 14 serves to maintain foam 11 stationary within capsule 12 and facilitates the nesting of the tampon on the insertion tube discussed with reference to FIG. 4. Necked region 14 may either be formed by the application of heat and pressure subsequent to the encapsulation of the foam, or may comprise the initial configuration of the capsule itself.

Figure 4:
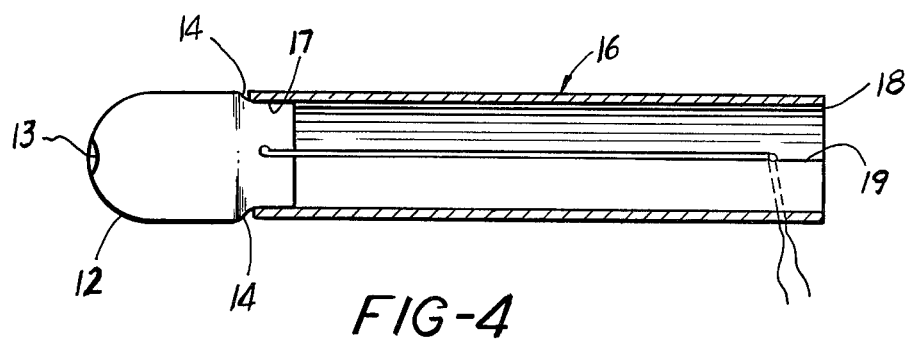
FIG. 4 is a side view partly in section showing the tampon of FIG. 3 mounted on a single insertion tube.

In FIG. 4, the tampon of FIG. 3 is mounted on an insertion means which comprises a single applicator tube 16. Applicator tube 16 is preferably cylindrical in shape and possesses an outer diameter approximately equal to the maximum outer diameter of capsule 12. Necked region 14 fits within one open end 17 of tube 16, and string 15 is situated so as to extend therethrough. The opposite end 18 of tube 16 is provided with a notch or slit 19 longitudinally extending a short distance along the side of the tube, which serves to frictionally engage string 15 and thereby maintain the tampon in fixed position on end 17. Thus, after insertion of the tampon into the vagina, string 15 is disengaged from notch 19, and tube 16 is then withdrawn.

Figure 5:
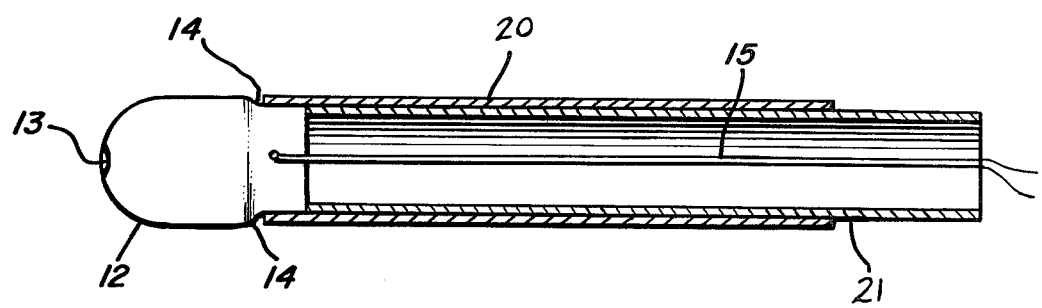
FIG. 5 is a side view partly in section showing the tampon of FIG. 3 mounted on telescoping insertion tubes.

Referring now to FIG. 5, the tampon of FIG. 3 is shown in full assembly prior to insertion, and is mounted on two insertion tubes, concentrically placed with respect to each other. Tube 20 is the outer tube and is the holder for the tampon. Tube 21 is the ejecting tube for inserting the tampon into the vagina. Tube 20 firmly grips the necked portion 14 of the tampon and prevents accidental removal from the holder. These tubes may be made from a variety of materials well known for this utility in the tampon art, such as cardbord, plastic, a combination of these materials, and the like.

The tampons described above may be employed as prepared, or may also contain, as desired, various suitable additives such as disinfectants, perfumes, medicaments, emollients, pigments and/or dyes. In a further emmbodiment, the tampons may be employed to test for the presence of various microorganisms, by the incorporation of a suitable chemical indicator. Naturally, the size and shape of the tampons of this invention may vary widely to account for variations in locus of use and functions.

The aspect of the invention relating to the rapid re-expansion of the foams of this invention will be illustrated by reference to the following example.

EXAMPLE

Hydrophilic polyurethane foam samples were pressed and held in compression for periods of time of 0 to 42 days to illustrate their speed of re-expansion. Samples were prepared by the respective impregnating techniques using powdered talc as the inorganic material. The precompressed foam measured 1 inch × 1 inch × 2 inches. The foam was compressed to fit within a gelatin capsule having a 0.5 inch diameter and a length of 0.75 inches. The capsule is open at one end and has a 0.125 inch diameter opening at the other end. The capsules were stored at the temperatures and the period of time set out in the Table, presented below.

TABLE

| Polyurethane Foam | Storage T° C. | Grams H₂O Uptake After 60-Second Soak at Number Days | | | | | |
|---|---|---|---|---|---|---|---|
| | | 0 Days | 3 Days | 7 Days | 14 Days | 28 Days | 42 Days |
| No additives | 25 | 46.5 | 46.9 | 42.0 | 27.6 | 17.3 | — |
| | 70 | 46.5 | 38.1 | 4.5 | 4.0 | 3.5 | — |
| Talc, eq. wt. to foam, applied as aqueous slurry | 25 | 46.9 | 46.2 | 49.2 | — | — | 49.2 |
| | 50 | | 51.0 | 41.4 | — | — | 31.7 |
| | 70 | | 46.0 | 29.7 | — | — | 9.2 |
| Talc, ½ wt. of foam, applied as aqueous slurry | 25 | 41.7 | 45.2 | 44.7 | — | — | 39.2 |
| | 50 | | 40.5 | 41.3 | — | — | 24.0 |
| | 70 | | 26.0 | 15.1 | — | — | 6.8 |
| Talc, ¼ wt. of foam, applied as aqueous slurry | 25 | 28.0 | 48.9 | 44.1 | — | — | 33.6 |
| | 50 | | 41.2 | 27.9 | — | — | 14.6 |
| | 70 | | 20.5 | 9.5 | — | — | 6.6 |
| Talc, eq. wt. to foam, applied dry | 25 | 17.5 | 47.0 | 44.0 | 42.5 | 21.7 | — |
| | 70 | 17.5 | 14.5 | 10.1 | 7.5 | 5.0 | — |

From the data presented above, relative to the uptake of water of the foam-containing gelatin capsule after a α-second soak, it can be seen that the foams prepared in accordance with this invention re-expand and take up water more rapidly. Water enters the cells of these foams at an accelerated rate to facilitate their improved expansion. Thus, after 28 days of storage at 25° C the polyurethane foam with no additives had an uptake of only 17.3 grams in a 60-second soak, while the talc impregnated foams had an uptake as high as 49.2 grams. The data at 70° C storage is similarly significant. It is very clear that the solid particulate agent significantly increases the ability of the foam to re-expand after storage in a compressed state.

Throughout the specification, all percentages of ingredients are expressed as percent by weight.

This invention may be embodied In other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed is:

1. A tampon assembly comprising:
a segment of compressed hydrophilic polymeric foam impregnated with about 10 to 200 percent by weight of an inorganic, water insoluble particulate material having an average particle size of about 0.1 to 100 microns and in compression to less than 50 percent of its original dry volume, wherein said solid particulate material is uniformly entrained within the cell structure of said hydrophilic foam and keeps the cell walls of said foam apart during compression, and prevents the formation of a bond therebetween, thereby facilitating the accelerated water uptake upon contact therewith;

a water soluble container substantially encasing and holding said segment in said compression along the entire length thereof, which provides lubrication for insertion of said segment into an animal's body cavity and is adapted for rapid disintegration therein; and removable insertion means axially communicating with said container to insert said segment into said body cavity.

2. The tampon assembly of claim 1 wherein said hydrophilic foam material is a hydrophilic polyurethane foam.

3. The tampon assembly of claim 1 wherein said compression ranges from about less than 25 to about less than 10 percent of said original dry volume.

4. The tampon assembly of claim 1 wherein said container comprises a capsule open at one end.

5. The tampon assembly of claim 4 wherein said capsule includes a segment adjacent said open end of reduced diameter defining a shoulder about the periphery of said capsule intermediate its ends.

6. The tampon assembly of claim 5 wherein said removable insertion means comprises at least one tube member and said capsule housing said segment is fitted within one end of said tube with said shoulder abutting said tube member.

7. The tampon assembly of claim 6 further including a withdrawal string fixed to said segment to facilitate removal of said tampon after use.

8. The tampon assembly of claim 7 wherein said removable insertion means comprises a single tube member, said segment and capsule are positioned on one end of said tube member and said withdrawal string extends through said tube member of the opposite end thereof, said opposite end provided with means to frictionally retain said withdrawal string whereby said string is retained under tension to fixedly secure said capsule and segment on said tube.

9. The tampon assembly of claim 4 wherein said capsule possesses a rounded configuration at the end opposite said open end, said rounded configuration including an access opening extended therethrough to facilitate contact of said segment by fluid impinging on the end of said capsule possessing said rounded configuration, to thereby initiate immediate absorption of fluid by said segment.

10. The tampon assembly of claim 1 said inorganic material is selected from the group consisting of talc, silica, alumina, clay, aluminosilicate, mica, asbestos, soapstone, magnesia, carbon black and baryte.

11. The tampon assembly of claim 1 further containing an additive selected from the group consisting of disinfectants, perfumes, emollients, medicaments, pigments and dyes.

12. A catamenial device comprising:

a segment of compressed hydrophilic polymeric foam impregnated with about 10 to 200 percent by weight of an inorganic, water insoluble, solid particulate material having an average particle size of about 0.1 to 100 microns and in compression to less than 50 percent of its original dry volume, wherein said solid particulate material is uniformly entrained with the cell structure of said hydrophilic foam and keeps the cell walls of said foam apart during compression, and prevents the formation of a bond therebetween, thereby facilitating the accelerated water uptake upon contact therewith; and a water soluble container substantially encasing and holding said segment in said compression along the entire length thereof, which provides lubrication for insertion of said segment into an animal's body cavity and is adapted for rapid disintegration therein.

13. The catamenial device of claim 12 further containing an additive selected from the group consisting of disinfectants, perfumes, emollients, medicaments, pigments and dyes.

* * * * *